United States Patent [19]

Chodorow

[11] 4,016,892
[45] Apr. 12, 1977

[54] DENTAL FLOSS HOLDER
[75] Inventor: Ingram S. Chodorow, Stamford, Conn.
[73] Assignee: Placontrol, Inc., Briarcliff Manor, N.Y.
[22] Filed: June 24, 1974
[21] Appl. No.: 482,131
[52] U.S. Cl. ............................................. 132/91
[51] Int. Cl.$^2$ ...................................... A61C 15/00
[58] Field of Search ............... 132/91, 89, 92 A, 93
[56] References Cited

UNITED STATES PATENTS

| | | | |
|---|---|---|---|
| 2,443,415 | 6/1948 | Buscarino | 132/91 |
| 2,981,264 | 4/1961 | Felice | 132/91 |
| 3,696,821 | 10/1972 | Adams | 132/91 |
| 3,744,499 | 7/1973 | Wells | 132/92 A |

Primary Examiner—G.E. McNeill
Attorney, Agent, or Firm—J. David Dainow

[57] ABSTRACT

The invention is a dental flossing device comprising a segment or strand of dental floss with two gripping means or grippers secured to the segment and spaced apart approximately three and a half inches. Preferably the grippers are small, flat tablet-like elements, having dimensions suitable to be gripped between two fingers of a user's hand; such grippers may be injection molded directly around or onto the floss. In manufacture, very long strands of dental floss will have such grippers secured along their length at selected intervals, and then packaged in a dispenser which allows removal from the long strand, of a single segment with two spaced grippers.

10 Claims, 17 Drawing Figures

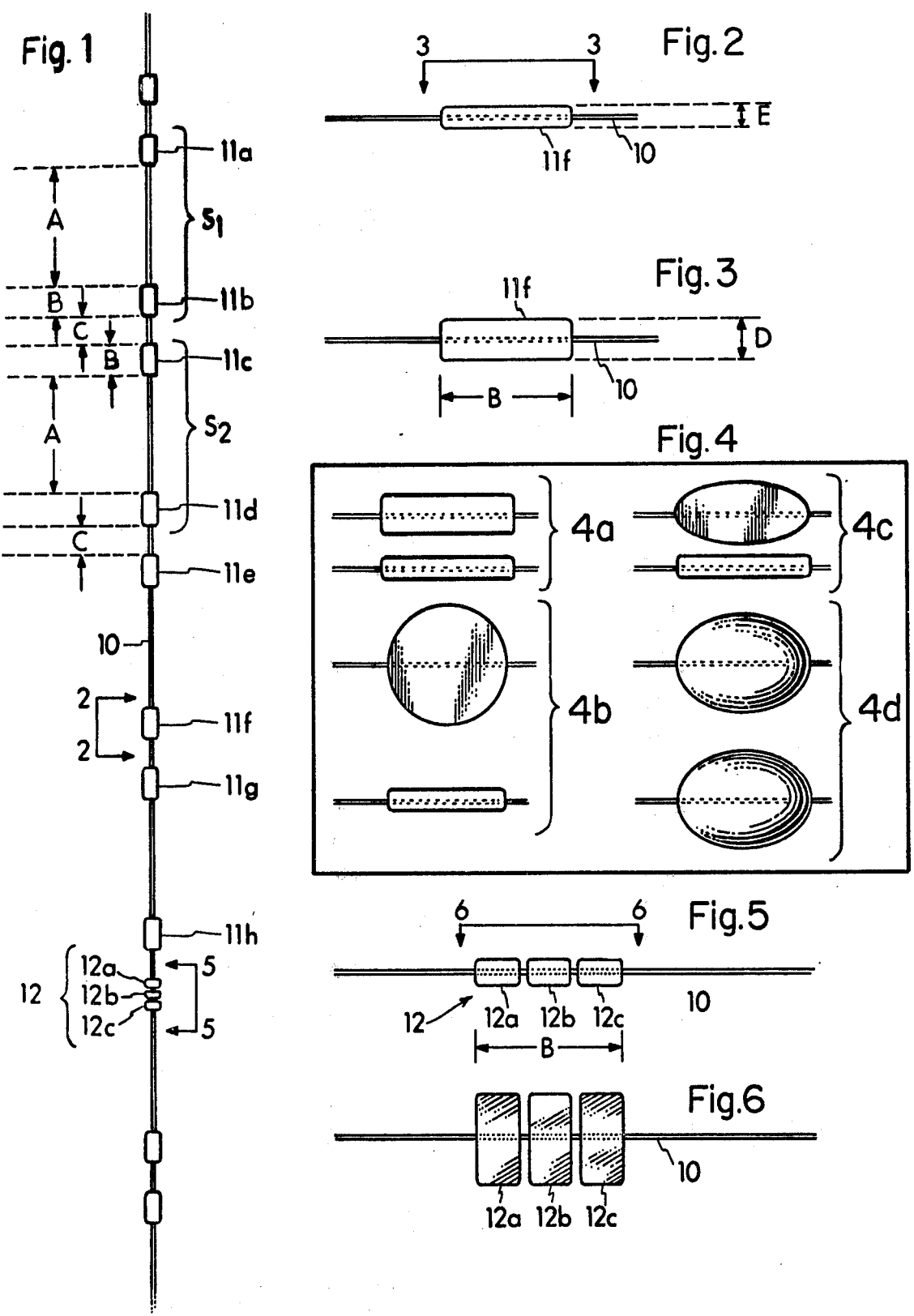

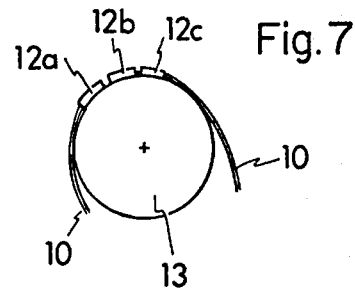
Fig. 7
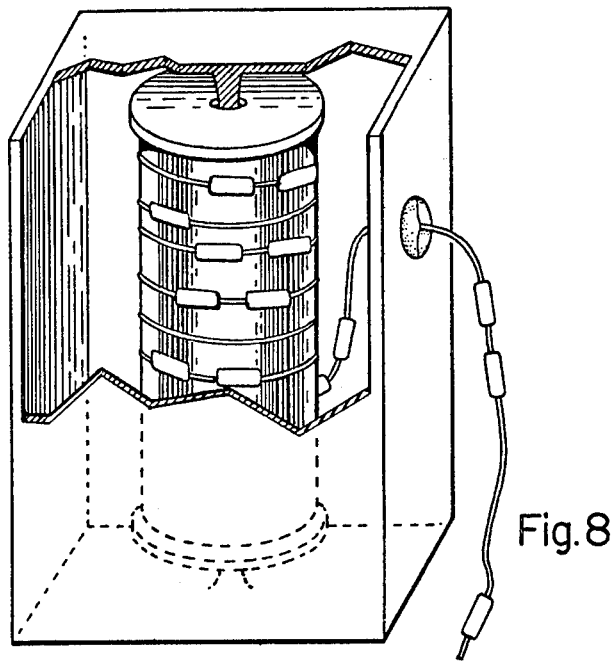
Fig. 8
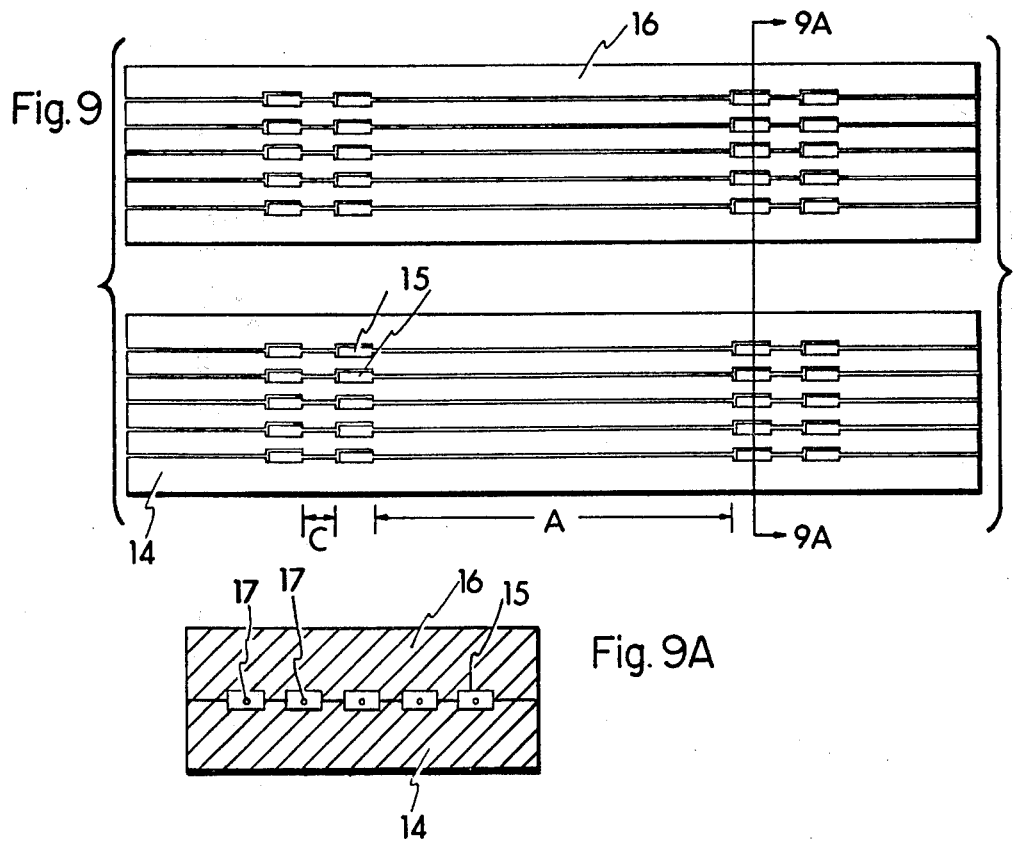
Fig. 9
Fig. 9A

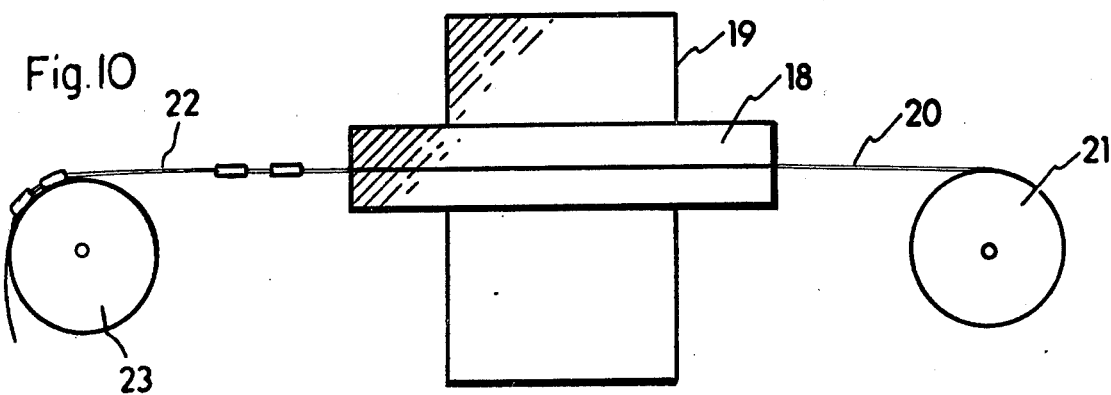
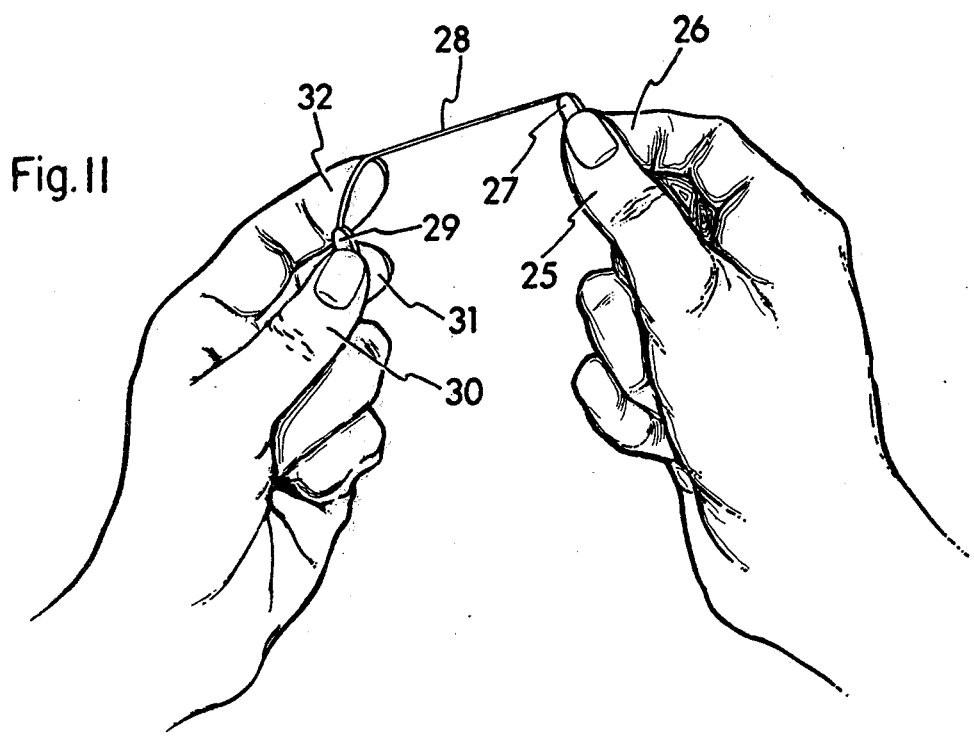

DENTAL FLOSS HOLDER

BACKGROUND OF THE INVENTION

This invention concerns dental floss and the manner in which it is used for preventative and corrective dental care. One particular type of dental floss, which is by far the most commonly used, is merely multi-filament nylon thread formed as a long strand that is generally packaged about a spool for easy dispensing. As advised by dentists and manufacturers, a typical user will sever an 18–30 inch segment, and then select a 2–3 inch section somewhere along the length, but inward from both ends; the floss on both sides of this section is wound tightly about fingers of both hands so that the section can be extended between the two hands in a generally well-known manner, and finally inserted into the space or tight crevice between two adjacent teeth. Once positioned, this section of floss is moved forward-and-backward against the tooth surface, either lengthwise or transverse of the tooth.

The purpose of flossing has been, for a very long time, primarily to remove debris from between two teeth or from between a tooth and the associated gum. It has recently been established that dental floss is very effective means for individuals to remove a substance called "plaque" from the teeth; it is important that such plaque be removed daily, because this substance is a most significant and damaging factor in the cause of tooth decay, gum disease, and periodontal disease which destroys supporting bony structure. Dentists of course, have sophisticated apparatus such as manual and powered scrapers and ultrasonic cleaners for removing plaque; however this substance can re-form noticeably within a twenty-four hour period. Since most people will not or cannot affort to visit their dentist daily, from a practical point of view persons wishing to protect and maintain their teeth will have to deplaque their own teeth regularly. While chemical mouth rinses for effortlessly dissolving plaque have been sought, none has been satisfactory; thus the only actual and practical method is to brush the exposed surfaces of the teeth with a toothbrush, and to floss the spaces between the teeth.

A more detailed definition of plaque is now helpful in order to understand the problem and subject of this invention. Plaque is a sticky substance which adheres to teeth as a filmy coating that becomes especially thick at the gum line and in the spaces between two adjacent teeth, which are not exposed to the mechanical cleansing motions of a toothbrush, the tongue, or the bathing action of saliva flow. Plaque is composed of food debris, bacteria, saliva and sloughed-off cells from gums or inner cheek surfaces, and if not removed, it develops into a cement-like tartar or calculus which must be scraped of by a dentist or dental technician. Calculus deposits are potentially serious hazards, as the precursors to gum problems and periodontal disease, which often results in loss of teeth.

The presence of plaque can be determined or felt by the tongue, especially on waking in the morning. Even after thorough brushing some plaque remains along the gum lines and in the interspaces where the brush could not reach. Such plaque can be readily observed by rinsing the mouth with a plaque-disclosing solution, which temporarily stains the plaque, and thus renders the plaque quite visible.

It has become readily apparent to persons associated with the dental health field, that dental floss is the most effective and most practical means for individuals to remove plaque daily and conveniently at home. In recent trade journals and trade conventions and in the market place, it is noted that a growing number of dentists and other persons in the dental field are not only promoting and urging greater use of dental floss, but are initiating extensive educational programs to teach the public about the danger of plaque accumulation on tooth surfaces and particularly in the crevices between adjacent teeth and areas between teeth and gums.

Flossing is thus becoming a widely practiced method of personal dental care; unfortunately however, such flossing, as presently known, has a variety of undesirable features which are generally accepted as inherent to the product and method and thus unavoidable, and these negative factors listed below, are acknowledged as the primary reasons why only 30% of the U.S. population uses dental floss with any regularity:

(1) Very young and very old people and may others simply do not have the dexterity, co-ordination, and/or strength to position the floss properly between the inter-dental spaces in their mouths, to manipulate their fingers and thus maneuver the floss as required.

(2) Another segment of the population finds objectionable the concept of putting their hands in their mouths and the likelihood of having and seeing food particles and other debris on their hands.

(3) Still another segment of the population who are willing to use the floss in the required manner, object to the fact that the floss will dig painfully into their fingers when wound and overlapped tightly, as is necessary to inhibit slipping of the floss; nylon floss is naturally slippery, and the popular wax-coated floss is even more slippery.

(4) Some persons feel that the use of floss in the normal manner constitutes a great waste, because while only a few inches or less are actually used, 2–10 times that length, typically 18–30 inches, must be cut to allow for winding both ends about the fingers.

(5) Finally some users object to the wax coating found on much of the floss that is sold. The wax apparently reduces fraying and provides a smoother outer surface; however this wax often becomes deposited on the user's fingers after the tightly wound floss is removed.

Dental floss, the subject matter of this invention, may take numerous forms besides multi-filament nylon; there are other synthetic materials, cotton thread, mono-filament thread, fishing line, metal wire, and even stretched rubber bands. Further alternative forms of floss are plain unwaxed floss, starched floss to render same somewhat stiffer and cohesive, waxed floss which also stiffens and reduces fraying, and dental-tape which is basically a strip or band of floss that is wider than thread but is approximately the same thickness.

Because of the intense and growing awareness that plaque is a serious problem, and that flossing is the only practical solution at this time, the use of dental floss is increasing and the floss market is expanding substantially. As indicated in the trade journals and trade shows, numerous companies are adding floss to their product line and are promoting the use of it. The amount of dental floss already in use is significant as indicated by retail sales in the United States of over $10,000,000.00, which at current prices represents approximately 1 billion yards of floss to be stretched between persons' fingers. In addition to Johnson and Johnson, the oldest and best known dental floss producer, other new trade-names of floss or floss distributors include P.O.H., Oral B, Kleen-Between, Butler, Control, Pycopay and Gudebrod.

The most remarkable fact about the above situation is that the floss sold by all of these companies is substantially identical in its structure and appearance. Furthermore, the manner of using floss has remained essentially unchanged for a great many years, especially including the present, namely, severing a floss segment and wrapping two spaced parts tightly about the fingers, so that the floss section between the fingers can be maneuvered down between two teeth and manipulated in various sawing motions against tooth surfaces. There has been essentially no innovation in this product and the manner of its use, except for certain floss holders which provide certain advantages but introduce new disadvantages, as will now be described.

A floss holder generally comprises a handle from which extends two spaced arms (sometimes like a slingshot); a segment of floss is extended across the space between the arms with the ends of the segment secured to one or more buttons on the handle. The user inserts the arm portions into his mouth until the floss is properly positioned at the beginning of a crevice between two teeth. By moving the handle he causes the floss to move down between the teeth to the gum. While this operation may for some persons be easier than the old method where ends of the floss are wound on the user's fingers, unfortunately floss holders have a variety of inherent limitations. The holder, whatever its shape might be, has a substantially fixed shape with a fixed distance between the arms; this distance is not the preferred distance by all people, and also is not the optimum distance for various different parts of the mouth. Obviously such handles with a fixed arm spacing and floss length cannot offer the variable distance and control that can be effectuated with one's own fingers. Another negative aspect of the holders is the cost of the handle over and above the cost of the floss used therein.

There are a variety of reasons why it is desirable to have floss available as a strand controlled by one's fingers, as opposed to floss mounted in a holder. But as is discussed above, such plain floss has a collection of its own inherent problems, that have as yet never been overcome. The new invention has the capability of overcoming most of the disadvantages of both the floss wound on fingers and of the floss in holders.

SUMMARY OF THE INVENTION

This invention comprises a long strand of dental floss of its equivalent with gripping means or elements or grippers secured on the floss at specified intervals. The grippers are preferably thin, flat objects approximately ½ inch long, positioned lengthwise along the axis of the floss. Typically there will be a floss length of approximately three inches between two grippers which defines a flossing unit, then a small length of floss, then another flossing unit, etc.. For convenience the floss will be contained in a dispenser, with the flossing units consecutively removed and severed from the dispenser.

In use one gripper will be held between two fingers in one hand, and the other gripper will be held between two fingers of the other hand. Then the floss will be inserted into the mouth, with the strand positioned between two teeth and then maneuvered down between the teeth. With the new device and new method I have eliminated the inconvenience of wrapping floss around the fingers in order to hold it securely, and obviously also eliminated the painful experience of tightly wrapped floss digging into the fingers is also avoided. Now only the actual length of floss to be used is required, as opposed to the extra lengths of floss required for wrapping. It will also be found that manipulation of the floss is far easier because with the grippers the usable span of floss extends from near the finger tips, as opposed to from the side of the finger where it lies from wrapping. Furthermore, much less physical effort and strain in the finger muscles and arms are required to hold the grippers than was required with the prior method of flossing. Because of these advantages the new floss device is now easily usable by many more persons, even those who could not previously use plain floss.

The manner of securing the gripper elements onto the floss may vary; but the preferred method is to injection mold these elements directly onto floss. Accordingly a mold cavity would have a long series of aligned cavities, and floss would be placed in alignment with these cavities prior to closing the mold. Then upon molding, the long strand with many elements along its length would be produced.

It is contemplated that a very good quality of nylon floss would be used which is multi-filament having two hundred or more filaments within each strand. It is also contemplated that the grippers would be made of nylon, however other plastics including polystyrene are feasible. Also of course the floss may be other materials such as cotton, rayon, etc. with nylon grippers molded onto nylon floss, the resulting nylon-to-nylon bond has been found to be most effective in assuring that the slippery floss will not be pulled out of the grippers in use.

The gripper elements may be secured to the floss by a great variety of methods, which include adhering the grippers after they are made, by adhesive or other mechanical means. Still another technique is to form both the grippers and the floss by injection molding, but this would probably be more costly than using premade floss. This invention also includes the method of manufacturing this new device and the manner of using same, as described in later paragraphs. The drawings described below disclose the invention in its preferred embodiments, but the invention may take various forms and thus is not limited to the exact configurations shown.

BRIEF DESCRIPTIONS OF THE DRAWINGS

FIG. 1 is a top plan view of the element, flossing along

FIG. 2 is an elevation view of one gripper elements, taken alone line 2—2 of FIG. 1.

FIG. 3 is a plan view of the element in FIG. 2, taken along line 3—3 of this Figure.

FIGS. 4a, 4b, 4c and 4d are each fragmentary plan and elevation views showing different shapes of grippers.

FIG. 5 is an elevation view of one gripper element, taken along line 5—5 of FIG. 1.

FIG. 6 is a plan view of the gripper in FIG. 5 taken along lines 6—6 of this Figure.

FIG. 7 is a fragmentary schematic view of a drum with a short length of the new floss device thereon.

FIG. 8 is a perspective view of dispenser containing a strand as in FIG. 1, wound on a drum.

FIG. 9 is an exploded, fragmentary view of an injection mold for producing strands as in FIG. 1.

FIG. 9a is a sectional view of the mold of FIG. 9 shown in closed position.

FIG. 10 is a schematic showing of a mold as in FIG. 9 operable with injection molding apparatus and drums of floss.

FIG. 11 is a schematic, elevation view of a flossing unit of this invention held by a user's hands.

DESCRIPTION OF THE PREFERRED EMBODIMENT

Figure 12:
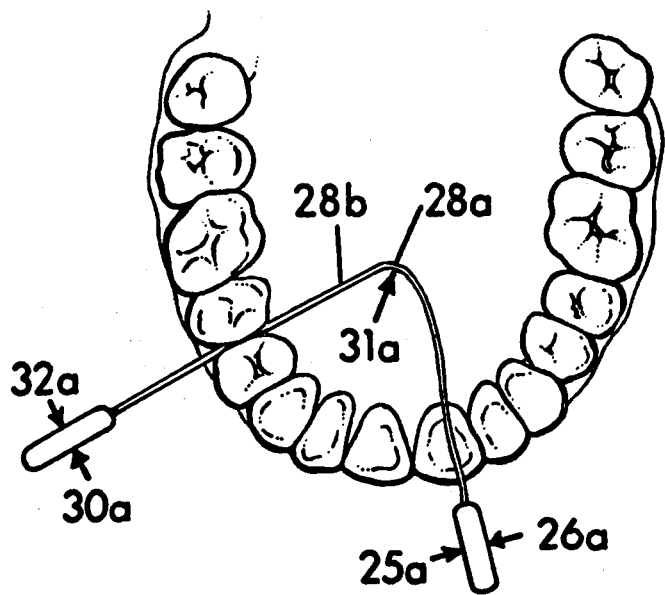
FIG. 12 is a schematic plan view of a flossing unit of this invention used in a persons's mouth.

FIG. 1 shows a strand of the new gripper floss according to this invention. A long, continuous strand of multi-filament nylon 10 has attached to it a plurality of solid plastic gripper elements or grippers 11. These elements are spaced in a pattern, wherein two typical elements 11a and 11b, separated by first distance A, define one usable flossing unit or segment $S_1$; a next adjacent unit $S_2$ is comprised of elements $11_c$ and $11_d$ separated by the same distance A. Each element has typical length B, and the second distance C separates each unit i.e. the space between 11b and 11c and between 11d and 11e.

It has been found that the following approximate lengths for the components of strand 10 provide a very satisfactory device: $A = 3$ inches, $B = ½$ inch, and $C = ½$ inch wherein A is substantially greater than C. In use, consecutive units would be separated, as $S_1$ from $S_2$, by severing the floss in the area C, with other segments severed consecutively. A user would take one segment, $S_1$ for example hold element 11a between the thumb and forefinger of one hand, and element 11b between the thumb and forefinger of the other hand, and then be ready to floss his teeth.

A preferred gripper element is represented by items 11, 11a, 11b, etc. and 11f in FIGS. 2 and 3. Such elements have length, width and thickness dimensions, B, D, and E respectively, which are nominally ½ inch, ⅛ inch, and 1/16 inch, however numerous variations are obviously possible, with the element still being conveniently sized to be gripped securely between a thumb and finger. Certain of the other element shapes are disclosed in FIG. 4, where 4a shows plan and elevation views of a rectangular, flat element as in FIGS. 2 and 3; FIG. 4b shows an oval, flat element; FIG. 4c shows a round, flat element; and FIG. 4d shows a spherical element.

A somewhat different element shape 12 appears in FIGS. 5 and 6, where an element of length B (as in FIG. 3) is composed of three separate short elements 12a, 12b, and 12c, each of length ⅓B (or 1/6 inch) and spaced apart from each other a distance less than distance A between gripper elements. This provides substantially the same gripping surface as element 11f in FIG. 3; however element 12 has in effect three parts about two hinge joints which can bend around a small radius or drum 13 as in FIG. 7. This is desirable in packaging, where ½ inch long, non-bendable elements create limitations on the arrangement of this "new floss" and grippers situated within a dispenser, a sample of which is shown in FIG. 8.

The preferred method of manufacturing the new flossing device is with injection molding equipment of the type generally used to manufacture extremely high-volume items. FIG. 9 shows a portion of such a mold wherein the lower part 14 has a multiplicity of cavities for producing all the gripper elements, and upper part 16 has mating cavities. FIG. 9A shows a sectional elevation view of the mold of FIG. 9, when closed, with floss strands 17 extending lengthwise through the center of each cavity.

An operable injection molding apparatus is shown schematically in FIG. 10. The mold 18 is secured in the molding machine 19, with a source of standard floss 20 on drum 21, and the final product of floss with spaced grippers 22 being automatically wound on drum 23. With a mold having dozens of cavities, formed in numerous rows, it would be possible to run numerous strands simultaneously through the mold 18 at the appropriate cycle time for the machine and molding material to make hundreds of thousands of feet of "new floss" with grippers.

Gripper elements molded of nylon have been found to adhere very well to the nylon floss, and thus not slip during use; however numerous other plastics are feasible, including polystyrene, polycarbonate sold under the trademark LEXAN, and even rubber. Also various different materials may be used for the floss, including multi-filament nylon, rayon, dacron, and cotton, or other synthetic and natural fibers or combination thereof. Instead of molding the grippers directly onto the floss, it is also possible to make the elements separately, and secure them to floss by adhesive, solvent, melting, or some mechanical means as clamping, swaging, etc..

The manner of using this invention provides substantial advantages over the prior art method of winding plain floss on the fingers of both hands. FIG. 11 shows thumb 25 and forefinger 26 of a user's right hand with a gripper 27 between these fingers. Extending from gripper 27 is floss segment 28 to the other gripper 29 secured between fingers of the left hand. There are several different techniques for using this gripper floss: Essentially they involve holding the right gripper 27 with right hand fingers as shown, and holding the left gripper 29 with the left thumb 30 and the left middle finger 31 as shown, or between the thumb 30 and forefinger 32, similarly to the right hand. Now gripper 27 and the tips of right fingers 25 and 26 are inserted in the mouth, gripper 29 and the left hand fingers remain outside the mouth, and the floss 28 extends from outside to inside the mouth traversing the teeth and positioned to be maneuvered by a sawing motion between two adjacent teeth. Obviously left and right hands can be reversed.

An alternative technique for using the new gripper floss is shown schematically in FIG. 12 where the fingers are represented by arrows 30a and 32a for the left hand thumb and forefinger respectively, and 25a and 26a for the right hand thumb and forefinger, with the floss grippers held generally as in FIG. 11. However in FIG. 12 both grippers and fingers holding same are situated outside the mouth, while the tip of left index finger 31a is in contact with the floss near its mid-point 28a leaving clear part 28b of the floss between the left index finger contact 31a and the right hand fingers 30a and 32a. Now both right and left hand fingers holding the grippers and indicated by the arrows in FIG. 12, can remain outside the mouth, while finger 31a guides the floss between two teeth or elsewhere. In this method the index finger 31a of the left hand may be placed against the floss at various positions between the grippers to assist in proper positioning, and further to act as a fulcrum or lever for alternating tension and relaxation of the floss to accomplish insertion, wrapping, and sawing motions. Tension may be maintained on the full length of floss, even though it extends between three points, i.e. around a corner formed by finger 31a.

Figure 13:
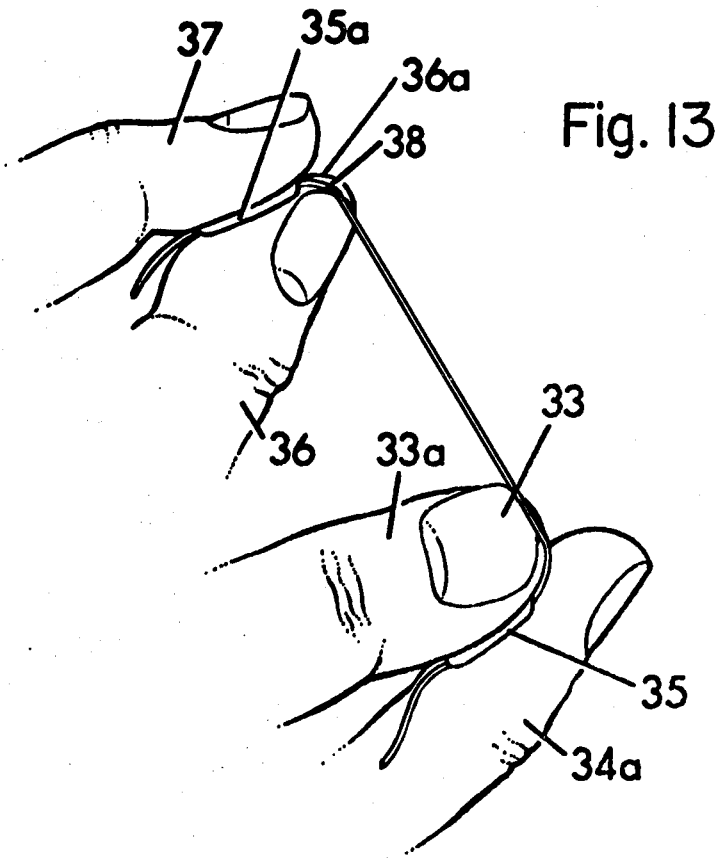
FIG. 13 is a schematic elevation view similar to FIG. 11.

With any of the above techniques, it will be quickly realized that one can hold the grippers securely and easily, with very little muscular effort. FIG. 13 shows that one can utilize the advantage of a finger nail 33 to help restrain gripper 35 between fingers 33a and 34a; also in this Figure, the gripper 35a is restrained partly by the friction induced by pressure applied by the fingers 36 and 37, but also by the additional friction developed where part 38 of the floss extends around the curved surface of thumb 36a. It is clear that with the arrangements of FIGS. 11, 12, and 13, I have completely avoided any prior art requirement of winding floss tightly about fingers of both hands, with the inherent discomfort and limitations in maneuverability due to the fact that the usable floss extends from a position on the side of the finger wherever the winding thereon stops. Now persons with less strength, dexterity, and/or ingenuity can floss their teeth more easily for the important dental health reasons. The need to put one's fingers into his mouth is greatly reduced, mechanical advantages are gained in leverage and geometry, and finally of equal or greater significance is the fact that approximately 75% less floss is required with the elimination of winding on fingers of both hands. This is the first major innovation and change in dental floss and initial indications suggest a potential commercial success of sizable proportions.

This new invention as designed to be a commercial product and as generally shown in FIG. 1, comprises a continuous strand of dental floss with a plurality of gripping means secured to such strand and spaced apart from each other along the strand. These gripping means are positioned to define a plurality of consecutively spaced flossing units, each unit comprising a pair of said gripping means spaced apart from each other axially along the floss by a predetermined first length, A. For each two consecutive units, there are two adjacent gripping means which are spaced apart by a predetermined second length, C, less than the first length. Each of the gripping means is a three-dimensional member having dimensions suitable to be held between a thumb and a forefinger of a person's hand.

I claim:

1. A dental flossing apparatus formed as a plurality of consecutively spaced flossing units, the apparatus comprising a continuous strand of dental floss and a plurality of said flossing units secured to said strand, each of said flossing units comprising a pair of said gripping means, each of said flossing units spaced apart from adjacent units axially along said strand by a predetermined first distance, each two gripping means of each of said flossing units being spaced apart a second distance substantially greater than the first distance, each gripping means being a three dimensional member having length, axially along the strand, and width and thickness dimensions transversely of length suitable to be held between a thumb and forefinger of a person's hand, wherein said thickness and width are generally constant along the length of said gripping members.

2. Apparatus according to claim 1 wherein each gripping means comprises a plastic member injection-molded directly onto said floss and thereby fixedly secured thereto.

3. Apparatus according to claim 1 wherein each gripping means has dimensions of length, width, and thickness of approximately ½, ⅛, and 1/16 inch respectively, and said second and first distances are approximately 3 and ½ inches respectively.

4. Apparatus according to claim 1 wherein said second distance is in the range of 2 to 5 inches.

5. Apparatus according to claim 1 wherein each gripping means has a length dimension axially along said strand in the range of 1/16 to 6 inches.

6. Apparatus according to claim 1 wherein said floss is multi-filament nylon.

7. Apparatus according to claim 1 wherein said plurality of gripping means comprises only two, which constitute one pair of gripping means which with the floss thereby defines only one flossing unit.

8. Apparatus according to claim 6 wherein said gripping means are injection-molded nylon.

9. A dental device to be held between a person's fingers for flossing the person's teeth, comprising a continuous strand of dental floss and a plurality of gripping means secured to said strand and spaced apart from each other along said strand, said gripping means positioned to define a plurality of consecutively spaced flossing units, each unit comprising a pair of said gripping means, each of said units spaced apart from adjacent units axially along said strand by a predetermined first distance, each two adjacent gripping means of said flossing units being spaced part by a second distance substantially greater than said first distance, each gripping means being a three-dimensional member having length along said strand, and width and thickness dimensions transverse of length suitable to be held between a thumb and forefinger of said person's hand.

10. A device according to claim 9 wherein said gripping means each comprise at least two elements spaced apart from each other axially along said strand by a third distance less than said second distance.

* * * * *